(12) United States Patent
Connor (10) Patent No.: US 7,954,494 B1
(45) Date of Patent: Jun. 7, 2011

(54) DEVICE WITH ACTIVELY-MOVING MEMBERS THAT HOLD OR MOVE THE TONGUE

(76) Inventor: Robert A. Connor, Minneapolis, MN (US)

( * ) Notice: Subject to any disclaimer, the term of this patent is extended or adjusted under 35 U.S.C. 154(b) by 342 days.

(21) Appl. No.: 12/319,766

(22) Filed: Jan. 12, 2009

Related U.S. Application Data (60) Provisional application No. 61/070,755, filed on Mar. 26, 2008.

(51) Int. Cl.
*A61F 5/56* (2006.01)
*A61C 3/00* (2006.01)

(52) U.S. Cl. ............................................. 128/848; 433/6

(58) Field of Classification Search .................. 128/848, 128/860, 859, 861, 862; 602/902, 912; 433/6
See application file for complete search history.

(56) References Cited

U.S. PATENT DOCUMENTS

| | | | |
|---|---|---|---|
| 4,196,724 A | 4/1980 | Wirt et al. | |
| 4,304,227 A | 12/1981 | Samelson | |
| 4,676,240 A | 6/1987 | Gardy | |
| 4,978,323 A | 12/1990 | Freedman | |
| 5,046,512 A | 9/1991 | Murchie | |
| 5,154,184 A | 10/1992 | Alvarez | |
| 5,176,618 A | 1/1993 | Freedman | |
| 5,373,859 A | 12/1994 | Forney | |
| 5,465,734 A * | 11/1995 | Alvarez et al. ................ | 128/848 |
| 5,649,540 A | 7/1997 | Alvarez et al. | |
| 5,810,013 A | 9/1998 | Belfer | |
| 5,915,385 A | 6/1999 | Hakimi | |
| 5,921,241 A | 7/1999 | Belfer | |
| 5,950,624 A | 9/1999 | Hart | |
| 5,957,133 A | 9/1999 | Hart | |
| 5,988,170 A | 11/1999 | Thomas | |
| 5,988,171 A | 11/1999 | Sohn et al. | |
| 6,055,986 A | 5/2000 | Meade | |
| 6,244,865 B1 | 6/2001 | Nelson et al. | |
| 6,250,307 B1 | 6/2001 | Conrad et al. | |
| 6,267,591 B1 | 7/2001 | Barstow | |
| 6,295,988 B1 | 10/2001 | Sue | |
| 6,401,717 B1 | 6/2002 | Conrad et al. | |
| 6,408,851 B1 | 6/2002 | Karell | |
| 6,408,852 B2 | 6/2002 | Tielemans | |
| 6,450,169 B1 | 9/2002 | Conrad et al. | |
| 6,467,484 B1 | 10/2002 | De Voss | |
| 6,494,209 B2 | 12/2002 | Kulick | |
| 6,513,530 B2 | 2/2003 | Knudson et al. | |
| 6,513,531 B2 | 2/2003 | Knudson et al. | |
| 6,516,806 B2 | 2/2003 | Knudson et al. | |
| 6,523,542 B2 | 2/2003 | Knudson et al. | |
| 6,523,543 B2 | 2/2003 | Conrad et al. | |
| 6,601,584 B2 | 8/2003 | Knudson et al. | |
| 6,626,181 B2 | 9/2003 | Knudson et al. | |
| 6,634,362 B2 | 10/2003 | Conrad et al. | |

(Continued)

*Primary Examiner* — Patricia M Bianco
*Assistant Examiner* — Tarla R Patel (57) ABSTRACT

This invention is a device with actively-moving members external to the tongue that hold or move the tongue forward (using friction, compression, tension, pushing, pulling, adhesion, peristaltic motion, or a combination thereof) in order to reduce obstructive sleep apnea, snoring, or both. This device has advantages over Continuous Positive Airway Pressure (CPAP), surgical procedures, tubes or stents, jaw-positioning appliances, devices that use suction, piercing the tongue, and devices using friction with static or passively-moving members. With actively-moving members, the places of pressure on the tongue can be moved throughout the night to avoid tissue injury. Also, the device can actively re-engage tongue when it slips out. A dynamic sleep apnea device with actively-moving members creates new treatment options for the millions of people suffering from sleep apnea.

3 Claims, 7 Drawing Sheets

U.S. PATENT DOCUMENTS

| | | |
|---|---|---|
| 6,766,802 B1 | 7/2004 | Keropian |
| 6,848,447 B2 | 2/2005 | Conrad et al. |
| 6,877,513 B2 | 4/2005 | Scarberry et al. |
| 6,901,928 B2 | 6/2005 | Loubser |
| 6,935,335 B1 | 8/2005 | Lehrman et al. |
| 6,955,172 B2 | 10/2005 | Nelson et al. |
| 6,976,491 B2 | 12/2005 | D'Agosto |
| 7,028,691 B2 | 4/2006 | Knudson et al. |
| 7,036,515 B2 | 5/2006 | Conrad et al. |
| 7,047,979 B2 | 5/2006 | Conrad et al. |
| 7,063,089 B2 | 6/2006 | Knudson et al. |
| 7,073,505 B2 | 7/2006 | Nelson et al. |
| 7,073,506 B2 | 7/2006 | Robertson et al. |
| 7,100,613 B2 | 9/2006 | Conrad et al. |
| 7,107,992 B2 | 9/2006 | Brooks et al. |
| 7,137,393 B2 | 11/2006 | Pivovarov |
| 7,188,627 B2 | 3/2007 | Nelson et al. |
| 7,213,599 B2 | 5/2007 | Conrad et al. |
| 7,216,648 B2 | 5/2007 | Nelson et al. |
| 7,237,554 B2 | 7/2007 | Conrad et al. |
| 7,255,109 B2 | 8/2007 | Knudson et al. |
| 7,322,993 B2 | 1/2008 | Metzger et al. |
| 7,331,349 B2 | 2/2008 | Brady et al. |
| 7,337,781 B2 | 3/2008 | Vassallo |
| 7,363,926 B2 | 4/2008 | Pflueger et al. |
| 7,367,340 B2 | 5/2008 | Nelson et al. |
| 7,451,767 B2 | 11/2008 | Keropian |
| 2004/0045555 A1 | 3/2004 | Nelson et al. |
| 2004/0045556 A1 | 3/2004 | Nelson et al. |
| 2004/0049102 A1 | 3/2004 | Nelson et al. |
| 2004/0134491 A1 | 7/2004 | Pflueger et al. |
| 2004/0237965 A1 | 12/2004 | Bibi et al. |
| 2005/0133026 A1 | 6/2005 | Seleznev et al. |
| 2005/0150504 A1 | 7/2005 | Heeke et al. |
| 2005/0166929 A1 | 8/2005 | Jiang |
| 2005/0199248 A1 | 9/2005 | Pflueger et al. |
| 2005/0267321 A1 | 12/2005 | Shadduck |
| 2005/0268922 A1 | 12/2005 | Conrad et al. |
| 2005/0284485 A9 | 12/2005 | Nelson et al. |
| 2006/0005843 A9 | 1/2006 | Nelson et al. |
| 2006/0070626 A1 | 4/2006 | Frazier et al. |
| 2006/0130850 A1 | 6/2006 | Chen |
| 2006/0157055 A1 | 7/2006 | Pflueger et al. |
| 2006/0207606 A1 | 9/2006 | Roue et al. |
| 2006/0207608 A1 | 9/2006 | Hirotsuka et al. |
| 2006/0207612 A1 | 9/2006 | Jackson et al. |
| 2006/0266369 A1 | 11/2006 | Atkinson et al. |
| 2006/0270889 A1 | 11/2006 | Nelson et al. |
| 2006/0289013 A1 | 12/2006 | Keropian |
| 2007/0028926 A1 | 2/2007 | Kotani |
| 2007/0089756 A1 | 4/2007 | Nelson et al. |
| 2007/0102004 A1 | 5/2007 | Nelson et al. |
| 2007/0137654 A1 | 6/2007 | Paraschac et al. |
| 2007/0137655 A1 | 6/2007 | Paraschac et al. |
| 2007/0144532 A1 | 6/2007 | Gillis et al. |
| 2007/0144533 A1 | 6/2007 | Nelson et al. |
| 2007/0144534 A1 | 6/2007 | Mery et al. |
| 2007/0144539 A1 | 6/2007 | van der Burg et al. |
| 2007/0163603 A1 | 7/2007 | Sikora |
| 2007/0204866 A1 | 9/2007 | Conrad et al. |
| 2007/0209664 A1 | 9/2007 | Paraschac et al. |
| 2007/0261701 A1 | 11/2007 | Sanders |
| 2007/0267027 A1 | 11/2007 | Nelson et al. |
| 2007/0270631 A1 | 11/2007 | Nelson et al. |
| 2007/0272257 A1 | 11/2007 | Nelson et al. |
| 2007/0289600 A1 | 12/2007 | Li |
| 2008/0035158 A1 | 2/2008 | Pflueger et al. |
| 2008/0035160 A1 | 2/2008 | Woodson et al. |
| 2008/0041398 A1 | 2/2008 | Hegde et al. |
| 2008/0058584 A1 | 3/2008 | Hirotsuka et al. |
| 2008/0103545 A1 | 5/2008 | Bolea et al. |
| 2008/0161877 A1 | 7/2008 | Kirby et al. |
| 2008/0188947 A1 | 8/2008 | Sanders |
| 2008/0210244 A1 | 9/2008 | Keropian |
| 2008/0223367 A1 | 9/2008 | Cox et al. |
| 2008/0289637 A1 | 11/2008 | Wyss |

\* cited by examiner

DEVICE WITH ACTIVELY-MOVING MEMBERS THAT HOLD OR MOVE THE TONGUE

CROSS-REFERENCE TO RELATED APPLICATIONS

This patent application claims the priority benefit of provisional patent application Ser. No. 61/070,755 entitled "Automated tongue mover to reduce snoring or obstructive sleep apnea" filed on Mar. 26, 2008 by Robert A. Connor.

FEDERALLY SPONSORED RESEARCH

Not Applicable

SEQUENCE LISTING OR PROGRAM

Not Applicable

BACKGROUND

1. Field of Invention

This invention relates to tissue positioning devices to treat sleep disorders.

2. Related Art

Obstructive Sleep Apnea (OSA) is intermittent airflow blockage during sleep caused when the tongue and other soft tissue move backwards and block the airway. Numerous blockages happen during the night, resulting in poor quality sleep and intermittent oxygen deprivation. Approximately 20 million Americans and 35 million people worldwide have obstructive sleep apnea and the number is growing rapidly.

There are many direct and indirect harmful effects of obstructive sleep apnea. Potential harmful effects include: disrupted sleep; chronic fatigue; morning headaches; irritability; brain damage; cognitive dysfunction; impotency; high blood pressure; heart attacks; congestive heart failure; motor vehicle crashes; job-site accidents; and even death. Despite these harmful effects, it is estimated that only 5% to 8% of the affected population are treated.

Methods in the related art for treating obstructive sleep apnea include: Continuous Positive Airway Pressure (CPAP); surgical removal of soft tissue; surgical advancement of the jaw or tongue; surgical implantation of a tissue anchor; surgical implantation of a tissue stiffening implant; insertion of a tube or stent in the airway; electrical nerve and muscle stimulation; jaw-positioning appliances: non-dynamic tissue-positioning appliances using suction or friction; and other approaches (including magnets, tongue piercing, external body positioning structures, and pharmaceuticals). As we will now discuss, current applications of all of these approaches have significant disadvantages.

1. Continuous Positive Airway Pressure (CPAP):

Continuous Positive Airway Pressure (CPAP) is a means of keeping the airway open by constant positive air pressure. With CPAP, a machine continuously pumps positive pressure air (at a higher pressure than ambient air) into a mask that the sleeper wears on their face. The positive pressure keeps the airway open. CPAP is first-line therapy for the vast majority of people who are diagnosed with obstructive sleep apnea.

However, CPAP has many disadvantages and only a fraction of the people who are prescribed CPAP as therapy continue to use it. Disadvantages of CPAP include: wearing the mask can be very uncomfortable, limit freedom of movement during sleep, and cause a claustrophobic feeling; positive airway pressure can have a negative affect on exhaling and spontaneous respiration; the noise of the machine can disturb the patient or others in the same room; it is difficult to maintain a good seal of the mask to the face; it can dry out nasal passages and cause congestion; it can cause sore eyes, headaches, abdominal bleeding, chest muscle discomfort, nosebleeds and skin rashes; the machine can be expensive; and the machine can be difficult to transport when traveling.

2. Surgical Removal of Tissue:

An invasive approach to treating obstructive sleep apnea is surgical removal of tissue. Surgical treatments to remove tissue include: uvulopalatopharyngoplasty (UPPP)—removal of a portion of the soft tissue of the soft palate and/or pharyngeal walls; glossectomy—removal of a portion of the tissue of the tongue; and glossectomy. There are significant disadvantages with surgical tissue removal. It: is very invasive with relatively high failure rates and associated health risks; is irreversible; often causes significant pain and discomfort; is costly; has a long recuperative period; can cause speech impairment; can cause food and liquids to enter the nasopharynx during swallowing; and can even lead to episodes of choking.

3. Surgical Advancement of the Jaw or Tongue:

Another invasive surgical approach involves surgically moving structures and tissues forward, away from the airway. These surgeries include: mandibular advancement (in which the mandible is cut bilaterally posterior to the last molar and moved forward); maxillomandibular advancement (involving a portion of the jaw bone and teeth plus the portion of the skull to which the teeth are attached); and genioglossal advancement (pulling the genioglossus muscle in an anterior direction to bring the tongue forward). Disadvantages of such advancement surgeries include: its invasiveness; it does not always correct the problem; associated health risks; significant pain and discomfort; high cost; long recuperative period; potential speech impairment; and potential swallowing problems.

4. Surgical Implantation of a Tissue Anchor:

A third surgical approach involves implanting an anchor in soft tissue (such as the tongue), inserting a screw in a fixed structure in the mouth area (such as the base of the mandible), and then attaching them to each other (such as with a suture) to hold the soft tissue in position. Disadvantages of using tissue anchors for obstructive sleep apnea include: although less invasive than surgical removal of tissue, this still involves the costs and risks of surgery; results on effectiveness have been mixed; anchors can migrate in soft tissue and extrude from the tissue; pain and discomfort; speech impairment; and swallowing problems.

Related art involving surgical implantation of a tissue anchor includes U.S. Pat. Nos. 5,988,171 (Sohn et al.), 7,213,599 (Conrad et al.), 7,237,554 (Conrad et al.), 7,337,781 (Vassallo), and U.S. Patent Applications 20060207606 (Roue, Chad et al.), 20060207608 (Hirotsuka, Mark et al.), 20060207612 (Jackson, Jasper et al.), 20070144534 (Mery, Carlos et al.), 20070144539 (van der Burg, Erik et al.), 20070261701 (Sanders, Ira), 20080035160 (Woodson, Beverly et al.), 20080041398 (Hegde, Anant et al.), 20080058584 (Hirotsuka, Mark et al.), and 20080188947 (Sanders, Ira).

5. Surgical Implantation of a Tissue-Stiffening Implant:

Another surgical approach involves implanting a structure that stiffens soft tissue such as the soft palate or tongue. Disadvantages of using tissue-stiffening implants to treat obstructive sleep apnea include: although less invasive than surgical removal of tissue or a tissue anchor, this still involves the costs and risks of surgery; implants can extrude; and effectiveness of this approach for treating sleep apnea is still under investigation.

Related art involving implantation of a tissue stiffening implant includes U.S. Pat. Nos. 6,250,307 (Conrad et al.), 6,401,717 (Conrad et al.), 6,450,169 (Conrad et al.), 6,513,530 (Knudson et al.), 6,513,531 (Knudson et al.), 6,516,806 (Knudson et al.), 6,523,542 (Knudson et al.), 6,523,543 (Conrad et al.), 6,601,584 (Knudson et al.), 6,626,181 (Knudson et al.), 6,634,362 (Conrad et al.), 6,848,447 (Conrad et al.), 7,028,691 (Knudson et al.), 7,036,515 (Conrad et al.), 7,047,979 (Conrad et al.), 7,063,089 (Knudson et al.), 7,100,613 (Conrad et al.), 7,255,109 (Knudson et al.), 7,322,993 (Metzger et al.), and U.S. Patent Applications 20050268922 (Conrad, Timothy et al.), 20050284485 (Nelson, Lionel et al.), and 20070204866 (Conrad, Timothy et al.).

6. Tube or Stent:

In theory, an inserted tube or stent can keep the airway open. However, the airway has a lot of sensory innervation that causes reflex gagging and coughing in response to foreign objects. Related art involving insertion of a tube or stent in the airway includes U.S. Pat. Nos. 5,950,624 (Hart), 6,901,928 (Loubser), 6,976,491 (D'Agosto), 7,363,926 (Pflueger et al.), and U.S. Patent Applications 20040134491 (Pflueger, Russell et al.), 20050199248 (Pflueger, Russell et al.), 20060070626 (Frazier, Andrew et al.), 20060157055 (Pflueger, Russell et al.), 20080035158 (Pflueger, Russell et al.), and 20080223367 (Cox, Brian et al.).

7. Electrical Nerve and Muscle Stimulation:

An investigative approach to treating sleep apnea involves electrical stimulation of nerves or muscles that move soft tissue (such as the tongue) away from the airway. For example, the genioglossus muscle may be stimulated via electrodes on the mucosa on the floor of the mouth. This approach has potential advantages, but is not yet clinically proven and will involve the costs and risks associated with surgery. Related art involving electrical nerve and muscle stimulation includes U.S. Patent Applications 20080103545 (Bolea, Stephen et al.) and 20080161877 (Kirby, Todd et al.).

8. Jaw-Positioning Appliances:

Jaw-positioning oral appliances attach to the teeth. They hold the lower jaw forward to encourage forward movement of the tongue and soft palate. Disadvantages of jaw-positioning oral appliances include: they can cause TemporoMandibular Joint (TMJ) pain; they can be uncomfortable to wear and patient compliance is limited; they can be detrimental to the normal bite relationship of the dental arches; appliances that must be custom fitted are expensive; and forward positioning of the jaw does not always ensure forward positioning of the tongue and soft palate. Related art involving jaw-positioning appliances includes U.S. Patent Application 20080223367 (Cox, Brian et al.).

9. Non-Dynamic Tissue-Positioning Appliances Using Suction or Friction:

There are non-dynamic tissue-positioning appliances, without actively-moving members that hold or move the tongue, in the related art. Such non-dynamic appliances hold the tongue up, down, or forward using suction or friction. Disadvantages of appliances that use suction to hold the tongue include: when a patient swallows or otherwise moves their tongue, the vacuum can be broken and the wandering tongue may never be re-engaged in the device; and continuous suction can cause pain, swelling and edema in tongue tissue. The main disadvantage of non-dynamic appliances that use friction to hold the tongue is that—if they hold the tongue tightly then they are uncomfortable and the constant pressure points can injure tongue tissue, but if they hold the tongue loosely then the tongue can wriggle free during sleep and cause airway blockage.

Related art involving non-dynamic tissue-positioning appliances using suction or friction includes U.S. Pat. Nos. 4,196,724 (Wirt et al.), 4,304,227 (Samelson), 4,676,240 (Gardy), 5,154,184 (Alvarez), 5,373,859 (Formey), 5,649,540 (Alvarez et al.), 5,810,013 (Belfer), 5,915,385 (Hakimi), 5,921,241 (Belfer), 5,957,133 (Hart), 5,988,170 (Thomas), 6,055,986 (Meade), 6,244,865 (Nelson et al.), 6,267,591 (Barstow), 6,295,988 (Sue), 6,408,852 (Tielemans), 6,467,484 (De Voss), 6,494,209 (Kulick), 6,766,802 (Keropian), 6,877,513 (Scarberry et al.), 7,073,506 (Robertson et al.), 7,137,393 (Pivovarov), 7,367,340 (Nelson et al.), 7,451,767 (Keropian), and U.S. Patent Applications 20040045556 (Nelson, Lionel et al.), 20040237965 (Bibi, Noam et al.), 20050150504 (Heeke, David et al.), 20050166929 (Jiang, Yandong), 20060130850 (Chen, Haidong), 20060289013 (Keropian, Bryan), 20070028926 (Kotani, Hiroo), 20070289600 (Li, Kasey), 20080210244 (Keropian, Bryna), and 20080289637 (Wyss, Arthur).

10. Other Approaches:

There are a variety of other efforts to address obstructive sleep apnea, but many are still under investigation and they have not been shown to be effective and acceptable. These other approaches include: using magnetic implants to keep the airway open; piercing the tongue and anchoring the piercing member to an oral appliance; external devices to position the body such as chin straps, head straps and support pillows; and pharmaceutical treatments such as respiratory stimulants and tricyclic antidepressants.

Related art involving other approaches (including magnets, tongue piercing, external body positioning structures, and pharmaceuticals) includes U.S. Pat. Nos. 4,978,323 (Freedman), 5,046,512 (Murchie), 5,176,618 (Freedman), 6,408,851 (Karell), 6,935,335 (Lehrman et al.), 6,955,172 (Nelson et al.), 7,073,505 (Nelson et al.), 7,107,992 (Brooks et al.), 7,188,627 (Nelson et al.), 7,216,648 (Nelson et al.), 7,331,349 (Brady et al.), and U.S. Patent Applications 20040045555 (Nelson, Lionel et al.), 20040045556 (Nelson, Lionel et al.), 20040049102 (Nelson, Lionel et al.), 20060005843 (Nelson, Lionel et al.), 20050133026 (Seleznev, Katie et al.), 20050267321 (Shadduck, John), 20060266369 (Atkinson, Robert et al.), 20060270889 (Nelson, Lionel et al.), 20070089756 (Nelson, Lionel et al.), 20070102004 (Nelson, Lionel et al.), 20070137654 (Paraschac, Joe et al.), 20070137655 (Paraschac, Joe et al.), 20070144532 (Gillis, Edward et al.), 20070144533 (Nelson, Lionel et al.), 20070163603 (Sikora, Val J.), 20070209664 (Paraschac, Joseph et al.), 20070267027 (Nelson, Lionel et al.), 20070270631 (Nelson, Lionel et al.), and 20070272257 (Nelson, Lionel et al.).

To summarize the related art, all of the current approaches to treating obstructive sleep apnea have significant disadvantages. Obstructive sleep apnea remains a widespread condition with serious health consequences with inadequate treatment options. There remains a need for a less-invasive, more-effective, less-burdensome treatment for obstructive sleep apnea with fewer negative side effects.

SUMMARY

This invention is a device with actively-moving members external to the tongue that hold or move the tongue forward (using friction, compression, tension, pushing, pulling, adhesion, peristaltic motion, or a combination thereof) in order to reduce obstructive sleep apnea, snoring, or both.

Unlike Continuous Positive Airway Pressure (CPAP), this invention does not restrict sleeper movement by connection with an external hose and machine, does not have the continual noise of the air-pumping machine, does not dry out nasal passages, and is easily portable. Unlike various surgical procedures, this invention is non-invasive and reversible/removable during the day, reducing the risk of pain, speech impairment, and swallowing problems. Unlike tubes or stents, this invention does not engage the back of the tongue or throat and thus avoids reflex gagging and coughing. Unlike jaw-positioning appliances, this invention does not cause TMJ problems and it addresses the position of the tongue directly, rather than assuming that jaw movement ensures tongue movement. Unlike methods that require piercing the tongue, this invention is non-invasive. Unlike devices that use suction to hold the tongue in place, this invention does not create risk of tissue edema and does allow some tongue movement for greater comfort and less risk of tissue damage.

This invention with actively-moving members that hold or move the tongue using friction or compression also has significant advantages over non-dynamic devices that use static or passively-moving members to hold the tongue using friction or compression. For example, with non-dynamic devices that use static or passively-moving members to hold the tongue, if the frictional members successfully lock the tongue in place all night, then they press against the same spots on the tongue all night. There is no freedom of tongue movement for the sleeper and tongue tissue may be damaged at these spots of concentrated and prolonged pressure. However, with a dynamic device with actively-moving members such as proposed in this invention, the places of pressure on the tongue can be moved in a diffuse manner throughout the night. This can avoid tissue irritation and injury. By analogy, a patient who lies on a bed or sits in a chair in the same position all the time tends to get bed sores. A patient whose position on a bed or chair is shifted regularly, so that different points of tissue are in contact with the bed or chair over time, will be less likely to get bed sores.

Also, with non-dynamic devices that engage the tongue with friction or compression, if the tongue wriggles free from engagement with the device when the person swallows or otherwise moves their tongue during the night, then the tongue gets loose, is unlikely to reengage in the device, and airway blockage can result. However, with a dynamic device with actively-moving members to hold and move the tongue such as proposed in this invention, the device can actively re-engage tongue when it slips out.

Further, a dynamic device such as the one proposed herein gives the option of allowing freedom of tongue movement for extended periods of time and only actively engaging the tongue when necessary. Periods of freedom of movement for the tongue can make a big difference in acceptability to patients, as compared to a device that locks their tongue in the same place all night. By analogy, one could design an implantable cardioverter defibrillator that shocks people's hearts on a regular basis "just in case" they may have gone into ventricular tachycardia or fibrillation. However, such devices are actually designed to only shock the heart when needed—when ventricular tachycardia actually occurs. People do not want the discomfort of a device that shocks them at regular intervals, even if there is a chance that such shocks might, by chance, catch ventricular tachycardia before it would be shocked by a device that only activates when it detects ventricular tachycardia.

Relating this to analogy to sleep apnea, locking the tongue in place all night long is comparable to regularly shocking the heart. Both are uncomfortable. Both are avoidable with a dynamic system that only activates when needed. A dynamic implantable cardioverter defibrillator only shocks the heart when ventricular tachycardia is detected. A dynamic sleep apnea device may only engage the tongue when airway obstruction is detected. There are pros and cons with such a strategy. After study, it might turn out to be best to use an apnea device that engages the tongue constantly. However, it is worth investigating. A dynamic sleep apnea device such as the one proposed herein can open up new possible treatment options for the millions of people suffering from sleep apnea. To summarize, this invention is a novel and useful way to treat obstructive sleep apnea that has many advantages over approaches in the related art.

DRAWINGS

Introduction

FIGS. 1 through 7 show different examples of how this device may be embodied, but do not limit the full generalizability of the claims.

FIG. 1 also shows an example of this device that employs rotating belts and inflatable members.

FIGS. 3 through 5 show a cross-sectional perspective of a person's head with another example of the device, one with a series of inflatable members that push and pull the tongue forward using peristaltic motion.

FIGS. 6 and 7 show a cross-sectional perspective of a person's head with another example of the device. This example has a torus-shaped inflatable member that surrounds the tongue and pulls it forward.

DETAILED DESCRIPTION

FIGS. 1 through 7 show some examples of how this device may be embodied. However, many other embodiments are possible within the full scope of the claims.

Figure 1:
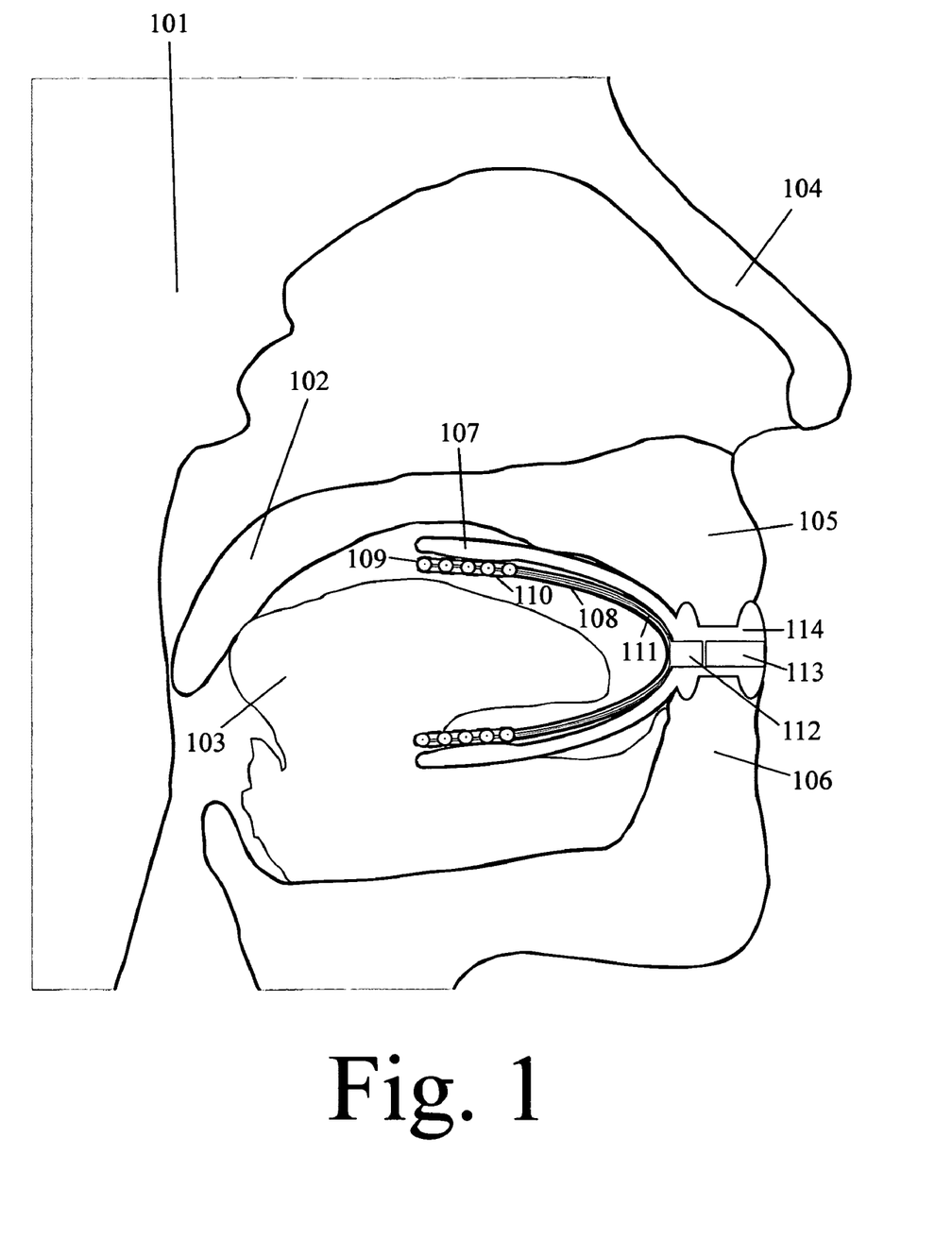
FIG. 1 shows a cross-sectional perspective of a person's head (including nasal cavities, mouth, and throat) during an episode of obstructive sleep apnea in which the tongue and soft palate are towards the back of the mouth and throat, blocking the airway.

FIG. 1 shows a cross-sectional perspective of a person's head during an episode of obstructive sleep apnea in which the tongue and soft palate are towards the back of the mouth and throat, blocking the airway. It also shows an example of the device within the mouth before device activation. Specifically, FIG. 1 shows the main body of the person's head 101, the soft palate 102, the tongue 103, the nose 104, the upper jaw 105 and the lower jaw 106. The tongue 103 is shown pushing back onto the soft palate 102 which blocks the airway between the soft palate 102 and the main body of the person's head 101.

In FIG. 1, there is an example of the device using both inflatable members and rotating friction belts. In this figure, the device is inserted into the mouth, but has not yet been activated. In this example, the device has: an inflatable outer parabolic member 107 with arms that curve over and under the tongue 103; and a flexible inner parabolic member 108 with arms that also curve over and under the tongue, but closer to the tongue than outer parabolic member 107. In a variation on this example, there may be two arms of each parabolic member under the tongue, one on either side, and two arms of each parabolic member over the tongue.

The outer parabolic member 107 has inflatable end portions that, when inflated by the action of inflation control unit 113, push the arms of flexible inner parabolic member 108 closer to the tongue. It pushes the top arm of inner parabolic member 108 downwards toward the top of the tongue 103 and the bottom arm of inner parabolic member 108 upwards toward the bottom of the tongue 103. In this example, inflatable members are made of relatively strong, but elastic, material such as latex rubber or a plastic elastomer. In this example, the inflatable members are inflated with air, but in an alternative example the members could be inflated with a liquid.

On the ends of each arm of the inner parabolic member are rotating friction belts 110 which are rotated in loops by rotating wheels 109. Rotating wheels 109 are driven by micro drive belts 111 which are powered by motion-creating member 112. In this example, the friction belts are made of durable, non-slippery material such as high-strength rubber. In this example, the motion-creating member is comprised of a small electric motor, battery, and microchip. Many small electric motors, batteries and microchips are known in the related art and the exact specifications are not central to the contribution of this invention that focuses on how the tongue is engaged and moved.

In this example, the motion-creating member 112 and inflation control unit 113 are housed within mouthpiece 114. Mouthpiece 114 is held in place by pressure from the lower jaw 106 and upper jaw 105. In a variation on this example, mouthpiece 114 may be further held in place by additional attachment to a strap that goes around head 101.

Figure 2:
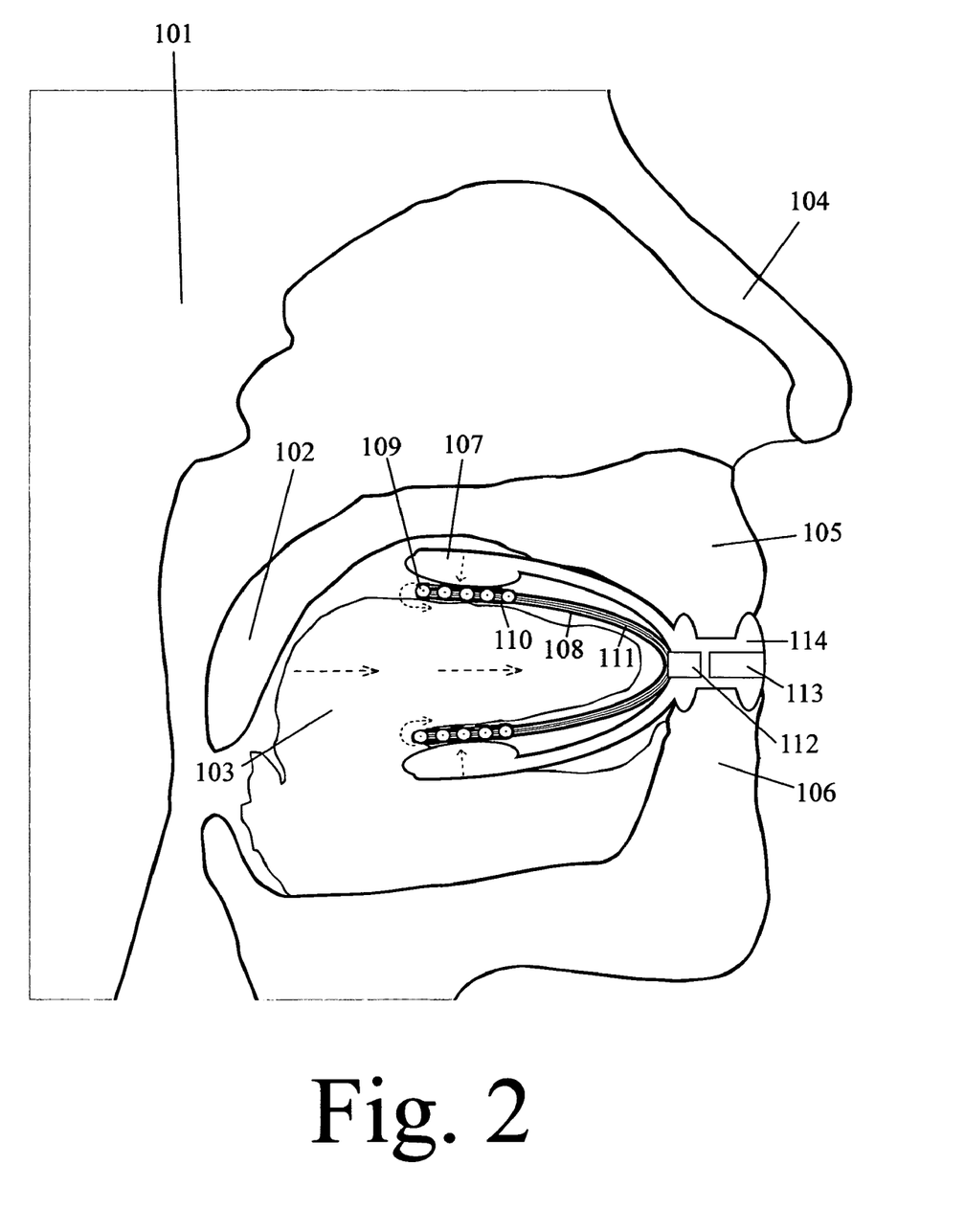
FIG. 2 shows this example as the rotating belts move the tongue forward to unblock the airway.

FIG. 2 shows the example device shown in FIG. 1 in automatic action, actively pulling the tongue 103 forward and unblocking the airway. Specifically, in FIG. 2, inflation control unit 113 pumps a flowable substance, air in this example, into the inflatable ends of the arms of outer parabolic member 107. This pushes the arms of flexible inner parabolic member 108 inwards toward the tongue 103 on both the top and bottom of the tongue. Concurrently, motion-creating member 112 rotates micro drive belts 111 which turn wheels 109 which rotate friction belts 110 on both the top and bottom of the tongue. The rotating friction belts 110 engage the surface of the tongue 103, pulling it forward and away from the soft palate 102. This helps to open the airway between the soft palate 102 and the main body of the person's head 101.

In this example, the rotating belts are relatively flat. In other examples, the rotating belts may have soft protuberances or brushes for additional friction and engagement of the tongue's surface. Automatic rotation of the belts may be continuous, periodic, intermittent, or triggered by sensors. The belts are designed so as to not harm to the tongue when it is fully drawn into the mouthpiece. In the morning, belt 110 motion can be turned off or reversed, and the outer parabolic member 107 deflated, to extract the tongue 103 and remove the device.

The combination of inflation of the outer parabolic member and the rotating belts on the inner parabolic member engage and pull the tongue more fully than can be done with the rotating belts alone. Automatic activation of these combined actions may be continuous, intermittent, periodic, or as needed based on sensor results indicating airway blockage.

There are several advantages of an automatically-moving system over a system that locks the tongue in the same position all night. First, changing the points of contact with the tongue over time can help reduce the risk of tissue irritation and injury. Second, unlike a static contact device, a system with active motion can re-engage the tongue in case the tongue slips out of engagement with the device during the night. Third, a system with active motion can be set to engage the tongue only when needed; this can give the wearer much more freedom of tongue motion as compared to systems that lock the tongue in place all night long. This latter point can be key to patient compliance with actually using the device.

Figure 3:
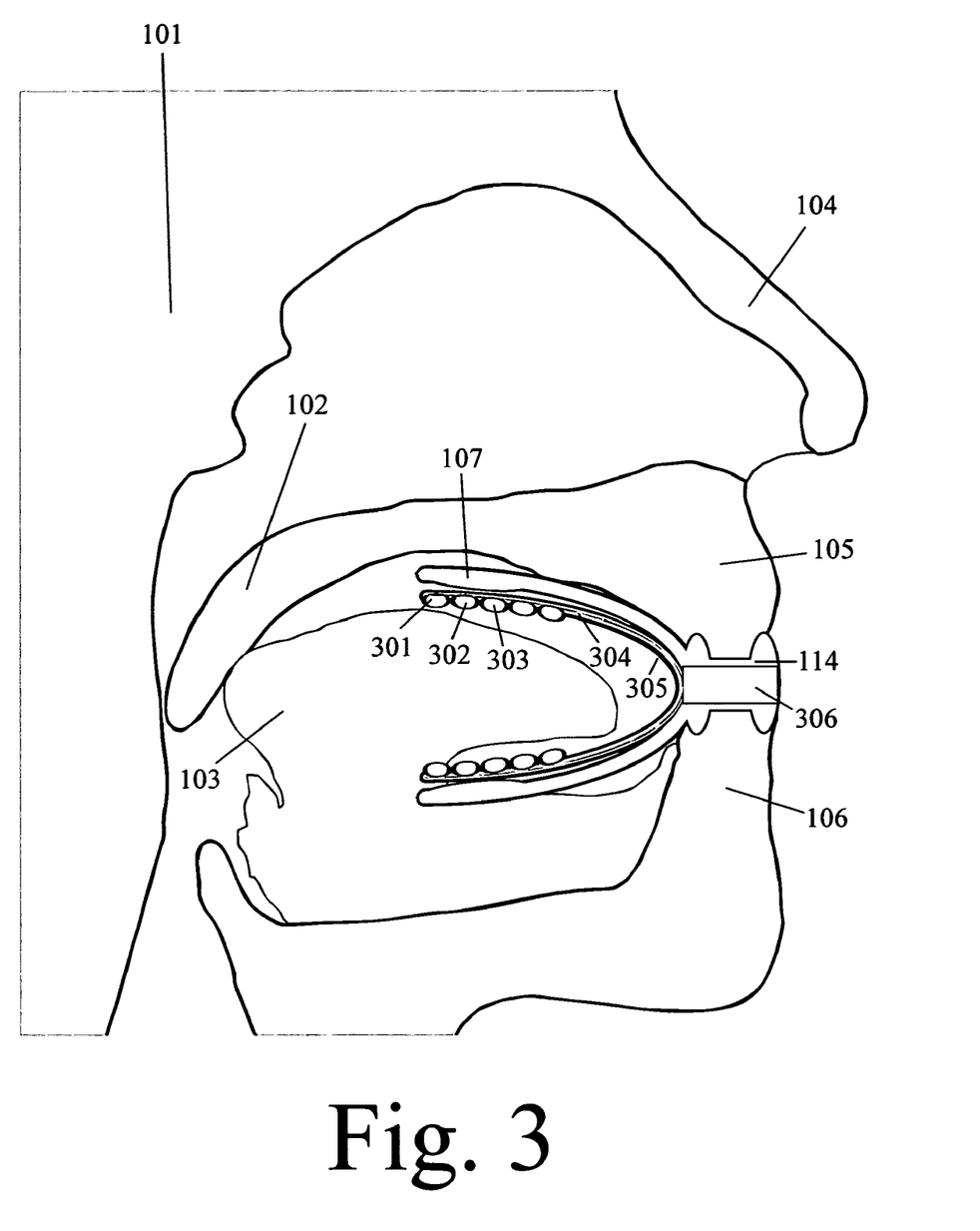
FIG. 3 shows airway blockage before the device moves.

FIG. 3 shows a cross-sectional perspective of a person's head with another example of the device. This example involves automated movement of a series of inflatable members that actively pulls the tongue forward during sleep using peristaltic motion. FIG. 3 shows a situation of airway blockage before the device activates. Specifically, FIG. 3 shows an example of the device with a series of sequentially-inflatable members, including 301, 302, and 303, attached to each arm of inner parabolic member 305. Each of these inflatable members is connected to a micro tube in micro tube bundle 304 that runs through the arms of parabolic member 305 to inflation control member 306 within mouthpiece 114.

Figure 4:
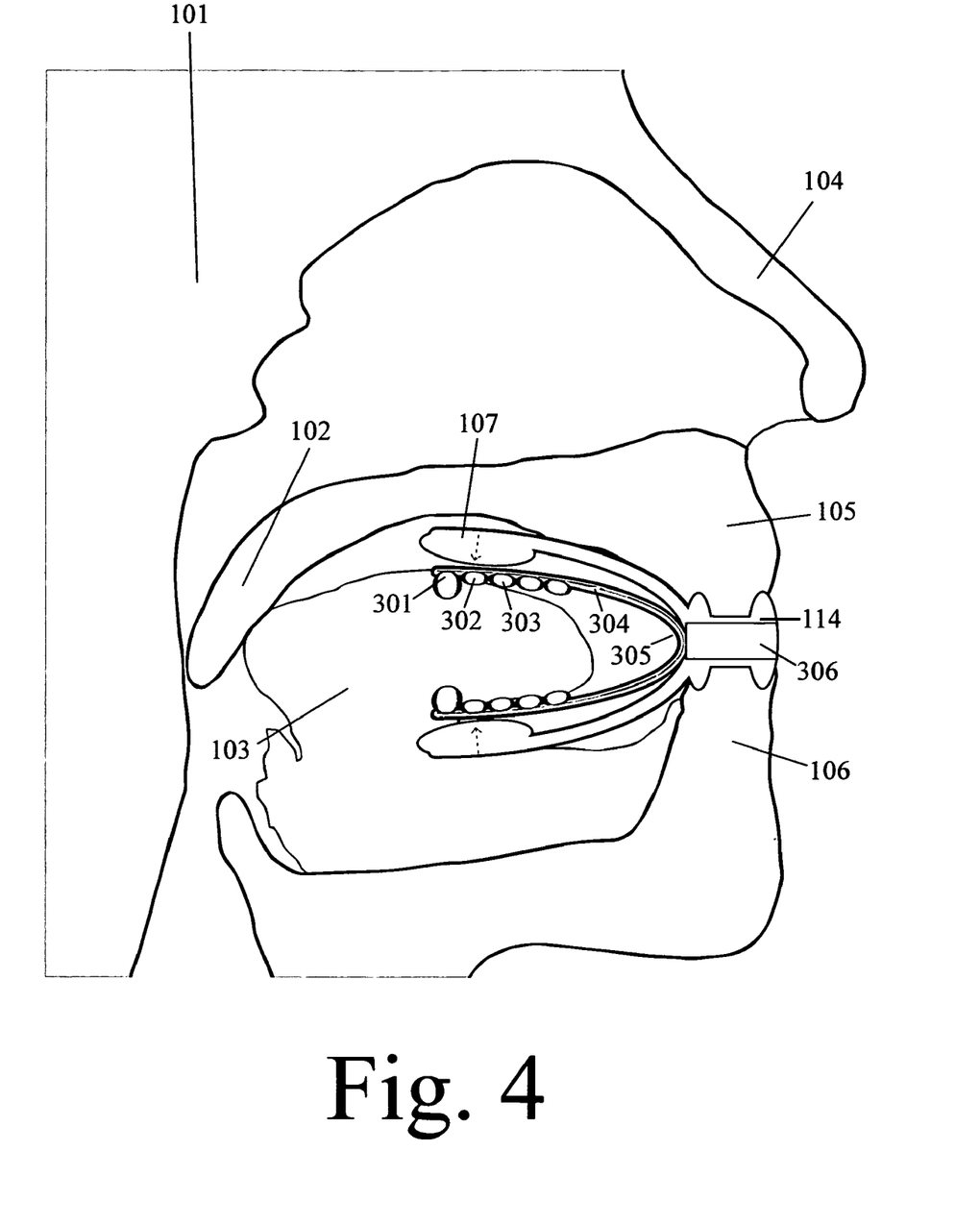
FIG. 4 shows the device as the first in a series of inflatable member inflates.

FIG. 4 shows the same situation and perspective as FIG. 3, except that: outer parabolic member 107 has been inflated; the first in the series of inflatable members 301 is inflated on the arm of the inner parabolic member over the tongue; and the corresponding inflatable member under the tongue is inflated as well. In this example, the inflatable members are made of relatively strong, but elastic, material such as latex rubber or a plastic elastomer. In this example, the inflatable members are inflated with air, but in another example they could be inflated with a liquid.

In FIG. 4, inflation of the arms of outer parabolic member 107 pushes the flexible arms of inner parabolic member 305 inward toward the tongue on both its top and bottom. This helps the inflatable members on inner parabolic member 305 to better engage the tongue. It can also allow the person to move their tongue relatively freely within their mouth until it is necessary to engage the tongue due to airway blockage.

In this automatic-inflation example of this device, the sequential inflation of the inflatable members is caused and controlled by inflation control member 306. Inflation of member 301 is the first step toward creation of a peristaltic wave to draw the tongue forward, but the peristaltic action is not yet complete so the tongue 103 remains pressed against the soft palate 102 in this figure. There are many ways to automatically pump air and electronically control pumping sequences in the related art, and the specifics are not central to the unique contribution of this invention, so they are not detailed here.

Figure 5:
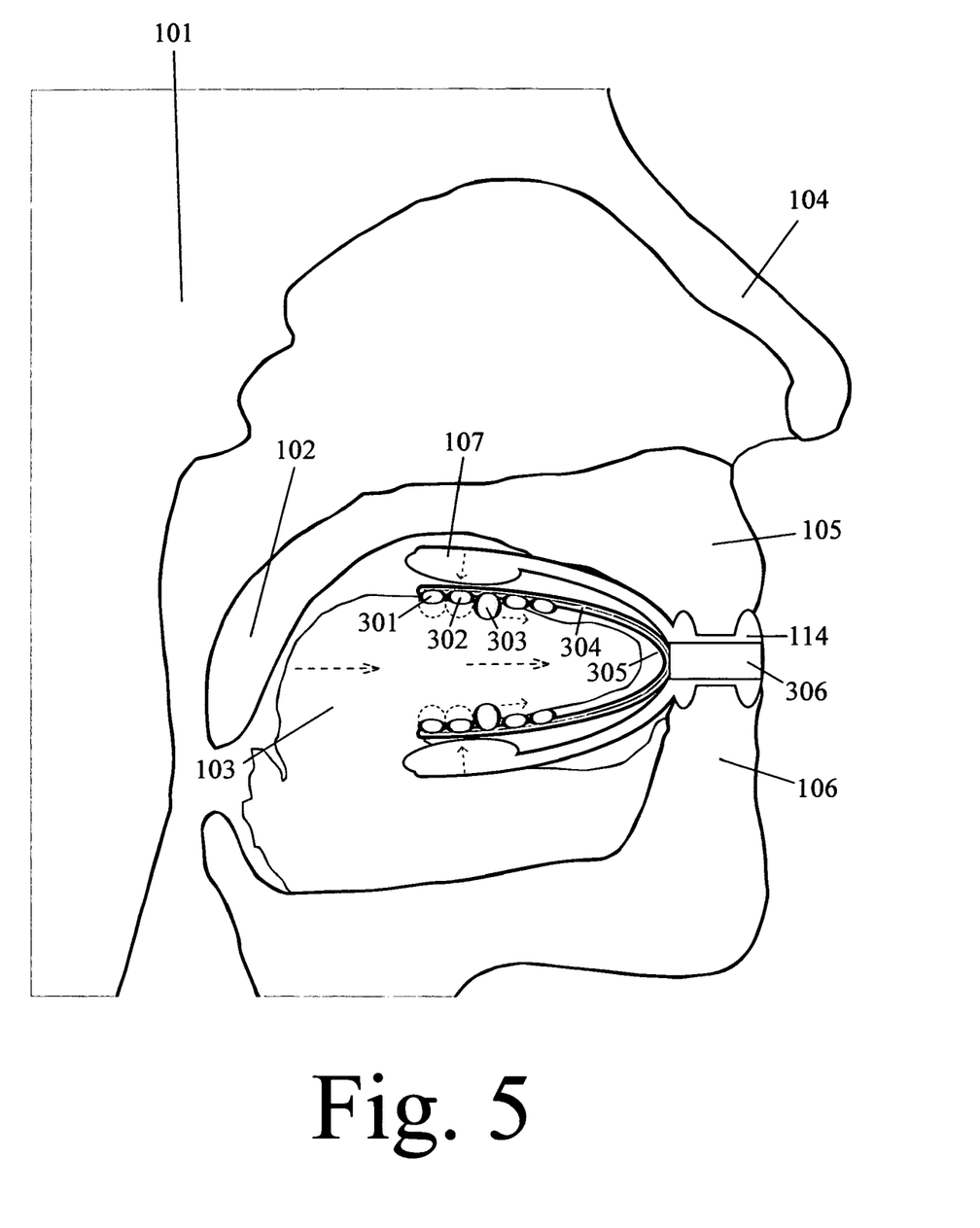
FIG. 5 shows a subsequent member having been inflated in a sequential progression that draws the tongue forward with peristaltic motion and opens the airway.

FIG. 5 shows the same perspective as FIGS. 3 and 4, except that now the peristaltic motion is fully underway with sequential inflation of inflatable members, drawing the tongue forward from the soft palate and opening the airway. Specifically, FIG. 5 shows inflatable members 301 and 302 as having inflated and deflated in sequence and shows inflatable member 303 as currently inflated. The resulting peristaltic motion pushes and pulls the tongue forward, which helps to open the airway. In an example, inflation of the outer parabolic member and peristaltic movement of the inflatable members on the inner parabolic member may be a constant cycle. Alternatively, it may be triggered in response to sensor results indicating that the air passage is blocked.

In this example, there is one series of sequentially-inflatable members over the tongue and the other series of sequentially-inflatable members under the tongue. In another example, there could be more than one series under the tongue, such as on either side of the tongue, and one or more series on top of the tongue.

Figure 6:
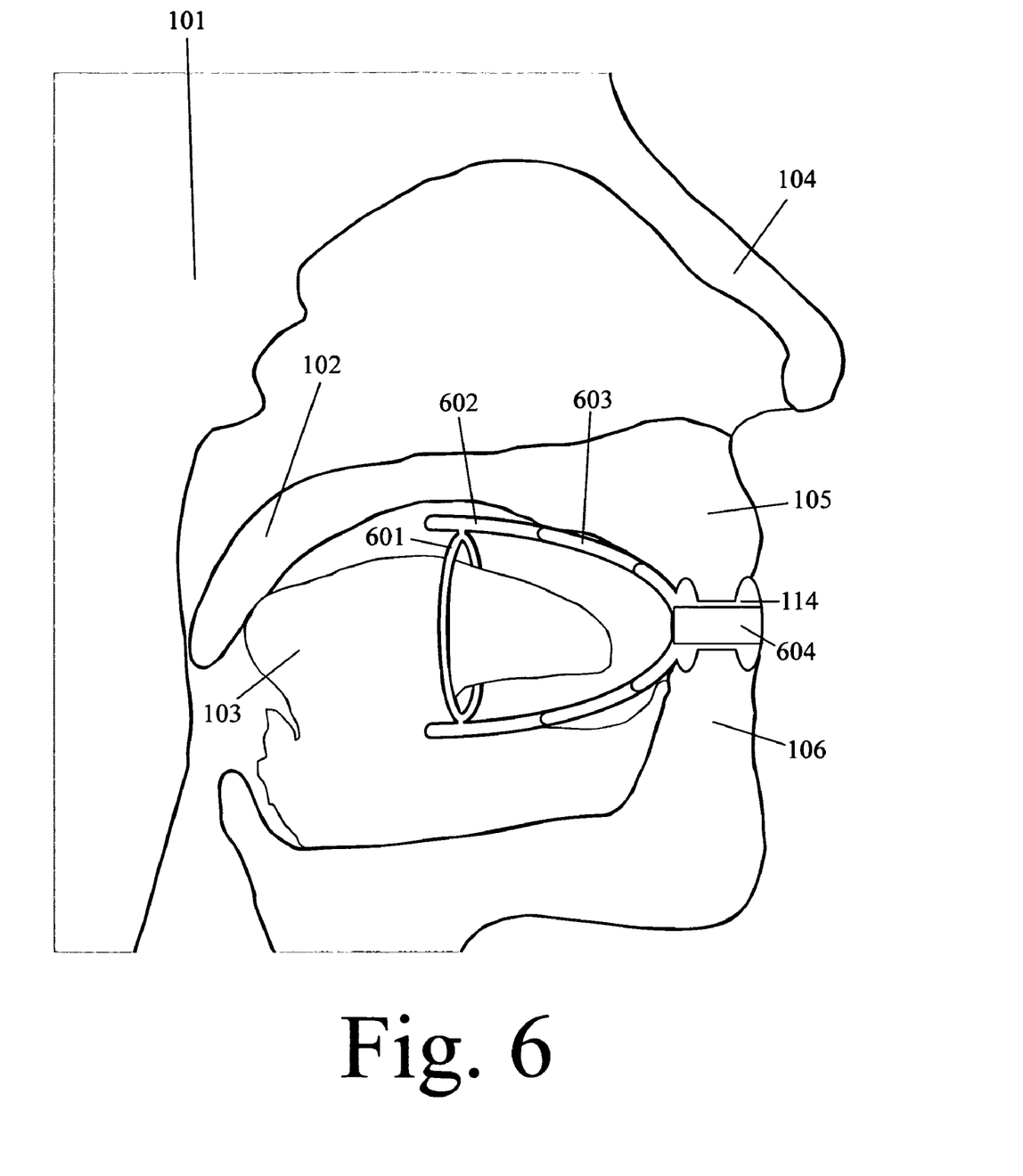
FIG. 6 shows airway blockage before the device moves.

FIG. 6 shows a cross-sectional perspective of a person's head with another example of the device with automated movement. In this example, there is a torus-shaped inflatable member 601 that surrounds the tongue 103. Before movement of the device, inflatable member 601 may be deflated so as to fit loosely around the tongue. This can allow considerable flexibility of the tongue during the night, until it is necessary to pull the tongue forward due to airway blockage. Torus-shaped inflatable member 601 is held in position by the arms of parabolic member 602 of the device.

Unlike parabolic members in prior figures, parabolic member 602 has a collapsible section 603 that can be hydraulically collapsed by control member 604. In this example, control member 604 includes an air pump, battery, and microchip. There are many variations of air pumps, batteries, and microchips in the related art and the specifics are not central to this invention that focuses on how the tongue is engaged and moved, so specifics are not included here. FIG. 6 shows airway blockage before the device is activated.

Figure 7:
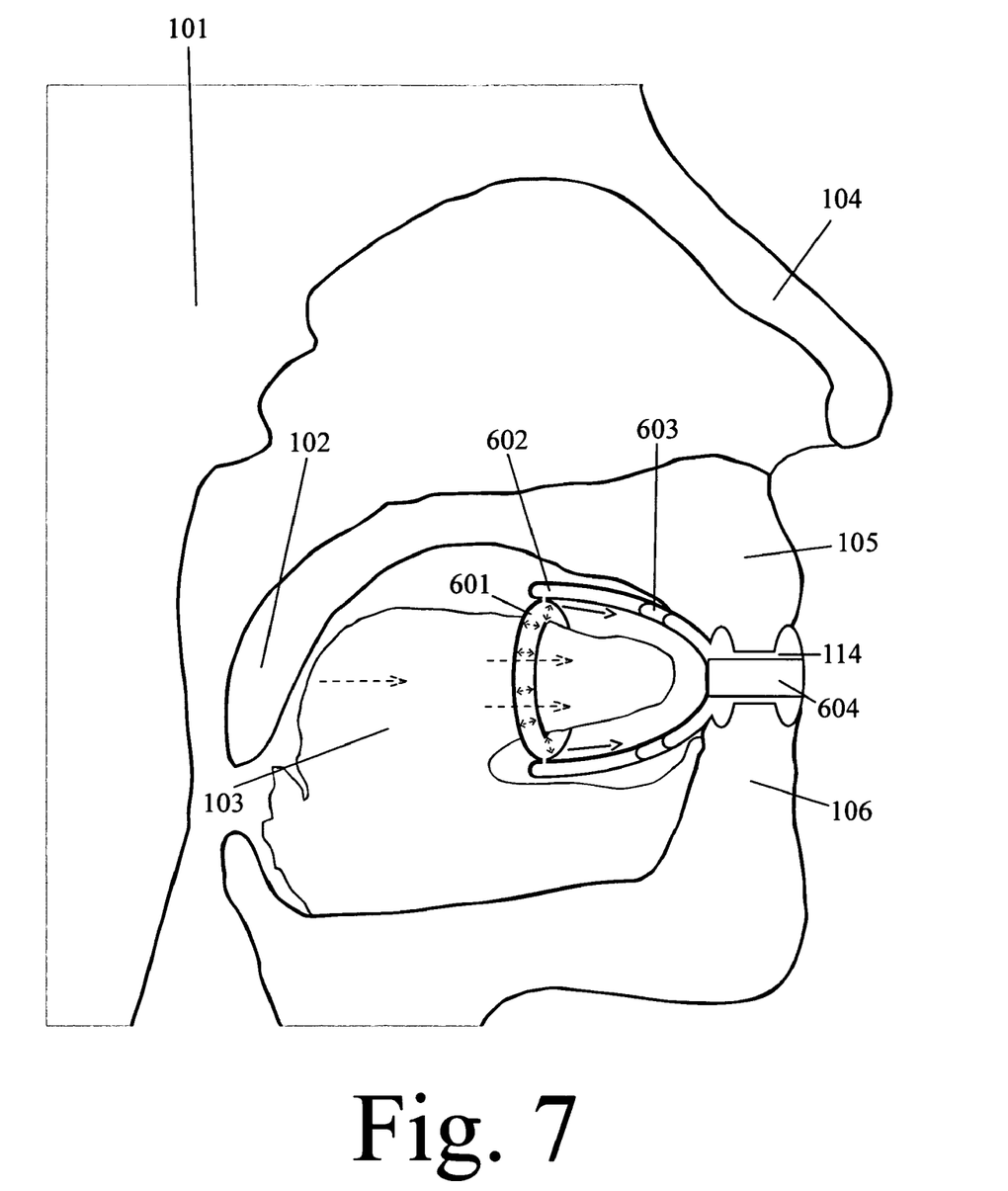
FIG. 7 shows inflation of the torus-shaped member around the tongue and forward movement of the tongue.

FIG. 7 shows inflation of the torus-shaped inflatable member 601 around the tongue and retraction of the arms 602 of the device by collapse of section 603. These combined actions engage and pull the tongue forward, which helps to open the airway.

I claim:

1. A device with actively moving members that hold or move the tongue comprising:
one or more actively moving and tongue-engaging members, wherein: these moving tongue-engaging members are external to the tongue but hold or move the tongue using friction, compression, tension, pushing, pulling, adhesion, peristaltic motion, or a combination thereof; and wherein the moving tongue-engaging members are sequentially-inflated pneumatic or hydraulic members that engage the tongue, with one set of members above the tongue and one set below the tongue, holding or moving the tongue between them with peristaltic motion;
and
one or more motion-creating mechanisms, wherein these motion-creating mechanisms actively move the tongue-engaging moving members while a person is sleeping so that the tongue-engaging moving members hold or move the tongue, thereby reducing obstructive sleep apnea, snoring, or both.

2. A device with actively moving members that hold or move the tongue comprising:
one or more actively moving and tongue-engaging members, wherein: these moving tongue-engaging members are external to the tongue but hold or move the tongue using friction, compression, tension, pushing, pulling, adhesion, peristaltic motion, or a combination thereof; and wherein the moving tongue-engaging members are balloons or other inflatable members that expand to engage the tongue, with one set of inflatable members above the tongue and one set below the tongue, holding or moving the tongue between them with compression, friction, pushing, and pulling;
and
one or more motion-creating mechanisms, wherein these motion-creating mechanisms actively move the tongue-engaging moving members while a person is sleeping so that the tongue-engaging moving members hold or move the tongue, thereby reducing obstructive sleep apnea, snoring, or both.

3. A device with actively moving members that hold or move the tongue comprising:
one or more actively moving and tongue-engaging members: wherein these moving tongue-engaging members are external to the tongue but hold or move the tongue using friction, compression, tension, pushing, pulling, adhesion, peristaltic motion, or a combination thereof; and wherein the moving tongue-engaging members are sequentially-inflated pneumatic or hydraulic members that engage the tongue, with one set of members above the tongue and one set below the tongue, holding or moving the tongue between them with peristaltic motion;
and
one or more motion-creating mechanisms, wherein these motion-creating mechanisms actively move the tongue-engaging moving members in an automatic manner while a person is sleeping so that the tongue-engaging moving members hold or move the tongue, thereby reducing obstructive sleep apnea, snoring, or both.

* * * * *